United States Patent
Mori et al.

(10) Patent No.: US 7,247,237 B2
(45) Date of Patent: Jul. 24, 2007

(54) FLUID CLEANING FILTER AND FILTER DEVICE

(75) Inventors: Hisashi Mori, Yokohama (JP); Tadashi Kuwahara, Yokohama (JP); Yasushige Shigyo, Yokohama (JP)

(73) Assignee: Bridgestone Corporation, Tokyo (JP)

( * ) Notice: Subject to any disclaimer, the term of this patent is extended or adjusted under 35 U.S.C. 154(b) by 0 days.

(21) Appl. No.: 10/889,251

(22) Filed: Jul. 13, 2004

(65) Prior Publication Data

US 2004/0262217 A1 Dec. 30, 2004

Related U.S. Application Data

(63) Continuation of application No. PCT/JP03/01112, filed on Feb. 4, 2003.

(30) Foreign Application Priority Data

Feb. 7, 2002 (JP) .............................. 2002-031050

(51) Int. Cl.
*B01D 29/07* (2006.01)
(52) U.S. Cl. .................... 210/338; 55/486; 55/488; 55/521; 210/493.1; 210/493.5; 210/497.01; 210/502.1; 422/177
(58) Field of Classification Search .......... 55/DIG. 39, 55/16, 485–489, 521, DIG. 13; 96/16; 422/24, 422/177; 210/493.1, 497.01, 502.1, 506, 210/337, 338, 493.5
See application file for complete search history.

(56) References Cited

U.S. PATENT DOCUMENTS

| | | | |
|---|---|---|---|
| 3,477,210 A * | 11/1969 | Hervert ........................ | 96/144 |
| 3,670,478 A * | 6/1972 | Welsh et al. .................. | 96/230 |
| 3,766,629 A * | 10/1973 | Lechtenberg ................ | 29/412 |
| 4,296,166 A | 10/1981 | Ogino et al. | |
| 5,820,644 A * | 10/1998 | Mori et al. ................. | 55/385.3 |
| 5,902,365 A * | 5/1999 | Haggard ....................... | 55/498 |
| 6,149,717 A * | 11/2000 | Satyapal et al. ............... | 96/16 |
| 6,277,176 B1 * | 8/2001 | Tang et al. ................... | 95/270 |
| 6,280,824 B1 * | 8/2001 | Insley et al. ................ | 428/172 |

(Continued)

FOREIGN PATENT DOCUMENTS

DE        40 23 995 A1       1/1992

(Continued)

OTHER PUBLICATIONS

Derwent Abstract for French patent 2,199,479.*

(Continued)

*Primary Examiner*—Joseph Drodge
(74) *Attorney, Agent, or Firm*—Sughrue Mion, PLLC (57) ABSTRACT

A fluid cleaning filter of the present invention consists of a composite matrix composed of a pleated substrate 2 configured into a pleated shape and an active carbon-containing layer 3, wherein the pleated substrate 2 is made of polyurethane foam 2a having a three-dimensional network skeletal structure, and the composite matrix is configured into a cylindrical shape. A filtering medium layer 2b made of fibers is formed on the surface of the polyurethane foam 2a facing the active carbon-containing layer 3. The fibers of the filtering medium layer maybe electrostatically charged. The fluid cleaning filter exhibits good efficiency of dust collecting and deodorization even when a fluid flows through the filter at high rate.

17 Claims, 6 Drawing Sheets

U.S. PATENT DOCUMENTS

| | | | |
|---|---|---|---|
| 6,514,324 B1 * | 2/2003 | Chapman | 96/67 |
| 6,986,842 B2 * | 1/2006 | Bortnik et al. | 210/232 |
| 2002/0037244 A1 * | 3/2002 | Takahashi et al. | 422/297 |
| 2002/0119723 A1 * | 8/2002 | Heinrich et al. | 442/389 |

FOREIGN PATENT DOCUMENTS

| | | |
|---|---|---|
| DE | 42 41 605 A1 | 6/1994 |
| EP | 0 803 275 A1 | 1/1997 |
| EP | 1 323 459 A1 | 7/2003 |
| FR | 2199479 * | 12/1974 |
| JP | 5-7725 A * | 1/1993 |
| JP | 09-276638 A | 10/1997 |
| JP | 10-043530 A | 2/1998 |
| JP | 10-174823 A | 6/1998 |
| JP | 2000-117021 A | 4/2000 |
| JP | 2002-028417 A | 1/2002 |
| JP | 2003-001028 A | 1/2003 |
| WO | WO 02/05927 A1 | 1/2002 |
| WO | WO 03/000382 A1 | 1/2003 |

OTHER PUBLICATIONS

U.S. Appl. No. 60/203,553, Bortnik et al, filed May 11, 2000.*
International Search Report.
International Search Report, Jan. 4, 2003.

* cited by examiner

FLUID CLEANING FILTER AND FILTER DEVICE

CROSS REFERENCE TO RELATED APPLICATION

This is a continuation application of PCT/JP03/01112 filed on Feb. 4, 2003.

FIELD OF THE INVENTION

The present invention relates to a fluid cleaning filter for cleaning a fluid, such as air, by filtering the fluid, particularly to a fluid cleaning filter suitably used in an apparatus in which a fluid flows at high rate, such as an air cleaner, room-air conditioner, especially vehicular ones, etc. The present invention also relates to a filter device employing the fluid cleaning filter.

BACKGROUND OF THE INVENTION

It is known in the art that a paper-like filter having functions to collect dust and to deodorize is configured in a pleated shape so as to increase its surface area, thereby improving its abilities to collect and capture dust and to deodorize, while reducing pressure loss. JPH10-43530 A has proposed an air cleaning filter utilizing a polyurethane form which has a three-dimensional network structure comprising of fine cells on one or both side(s) thereof.

JPH10-43530 A has further proposed a filter in which the polyurethane foam carries absorbent particles such as active carbon. However, the amount of the absorbent particles is relatively small, so that lack of deodorizing feature might occur in some instances.

SUMMARY OF THE INVENTION

The fluid cleaning filter of the present invention includes a composite matrix composed of a pleated substrate configured into a pleated shape and an absorbent-containing layer, wherein the pleated substrate is made of polyurethane foam at least a part of which has a three-dimensional network skeletal structure, and the composite matrix is configured into a cylindrical shape.

The filter device of the present invention is equipped with the fluid cleaning filter of the present invention.

BRIEF DESCRIPTION OF THE DRAWINGS

FIGS. 1a, 1b and 1c illustrate a fluid cleaning filter according to an embodiment of the present invention, where

FIGS. 2a and 2b illustrate a pleated substrate of a fluid cleaning filter according to an embodiment of the present invention, where FIG. 1a shows a perspective view of a corrugated sheet-like pleated substrate 2' and a flat sheet-like absorbent-containing layer 3', and FIG. 1b shows a side view of a flat sheet-like filter 1' before configured into cylindrical shape.

DETAILED DESCRIPTION OF THE PREFERRED EMBODIMENTS

A fluid cleaning filter of the present invention includes a pleated substrate made of polyurethane foam and an absorbent-containing layer. The absorbent-containing layer can contain a sufficient amount of absorbent, so that the filter can exhibit very good efficiencies of dust collection and deodorization. In the filter of the present invention, the polyurethane foam need not carry the absorbent, thereby reducing pressure loss even when the filter is employed in an apparatus in which a fluid is driven at high rate, such as a vehicular air conditioner.

The filter of the present invention is suitable for filtration of gas, including air, while it can be also used for filtration of liquid.

The absorbent-containing layer may carry a catalyst (for example, photocatalyst) to decompose substances absorbed by the absorbent. The catalyst prevents the absorbent, such as active carbon, from being saturated with the absorbed substances, thereby improving the fluid cleaning filter in the efficiency of absorption.

The absorbent-containing layer may include or consist of a material (substrate) having fluid-permeability, including gas-permeability, and the absorbent carried by the material.

The material may have a three-dimensional fibrous skeletal structure in which a pair of two-dimensional fibrous skeletal structures are disposed in parallel to each other at a cirtain spacing and connected together with myriad connecting threads. The three-dimensional fibrous skeletal structure composed of two-dimensional fibrous skeletal structures can be flexibly deformed into a cylindrical shape by winding it. That is, the three-dimensional fibrous skeletal structure can be easily deformed into a cylindrical shape without buckling or crushing. This structure can carry an extremely sufficient amount of the absorbent.

In the present invention, a filtering medium layer made of fiber material may be provided on the surface of the pleated substrate made of polyurethane foam. With the filtering medium layer, the filter can capture fine particles which the polyurethane foam can not capture. The filtering medium layer may be located on the downstream side surface of the polyurethane foam. For example, in case that the absorbent-containing layer is configured into a cylindrical shape and located inside the pleated substrate coaxially, and a fluid flows from the outside to the inside of the filter, the filtering medium layer made of fiber material is located on the inside surface of the pleated substrate, facing the absorbent-containing layer.

The fiber material may include or consist of synthetic fibers or glass fibers. When the fiber material is electrostatically charged, the filtering medium layer can capture fine particles very efficiently.

The filtering medium layer made of fiber material may have a nonwoven fabric layer. The filtering medium layer may have a fiber netting and a nonwaven fabric layer interlocked to the netting.

The pleated substrate may be configured into a cylindrical shape in such a manner that the pitch direction between the pleats thereof is oriented to the circumferential direction of the cylinder and the absorbent-containing layer may be also configured into a cylindrical shape so as to be attached to the cylindrical pleated substrate coaxially. The cylindrical absorbent-containing layer may be located along the inner circumferential surface of the cylindrical pleated substrate. In this case, a fluid, such as air, first permeates through the pleated substrate from the outside thereof so that dust contained in the fluid is captured thereby, and then the fluid permeates through the absorbent-containing layer so that the fluid is further applied with advanced treatments including deodorization.

The cylindrical absorbent-containing layer may be located inside the pleated substrate and integrated with the pleated substrate. In this case, the pleated substrate is reinforced with the absorbent-containing layer.

The number of cells (pores) in the polyurethane foam per one inch may be 6 to 80 PPI (pores per inch).

A filter device of the present invention contains the filter of the present invention. In case that the absorbent-containing layer of the filter carries photocatalyst, the filter device may also contain a means for irradiating light (for example, ultraviolet light) to the absorbent-containing layer.

In case that the absorbent-containing layer of the fluid cleaning filter is located along the inner circumferential surface of the cylindrical pleated substrate, the light irradiating means may be located inside the absorbent-containing layer.

In case that the material comprising the absorbent-containing layer has the three-dimensional fibrous skeletal structure in which a pair of two-dimensional fibrous skeletal structures are disposed in parallel to each other at a cirtain spacing and connected together with my riad connecting threads, sufficient light permeates into the absorbent-containing layer, thereby improving activity of the photocatalyst.

Hereinafter, embodiments of a fluid cleaning filter and filter device according to the present invention will be described in detail with reference to the drawings, while the present invention is not limited to the configuration shown in the drawings and may be applied with any modifications.

Figure 1A:
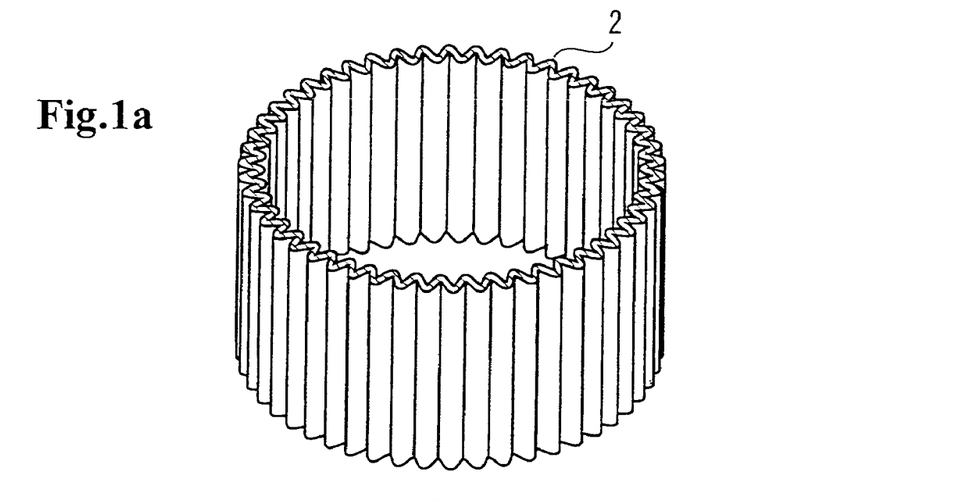
FIG. 1a shows a perspective view of a pleated substrate.
Figure 1B:
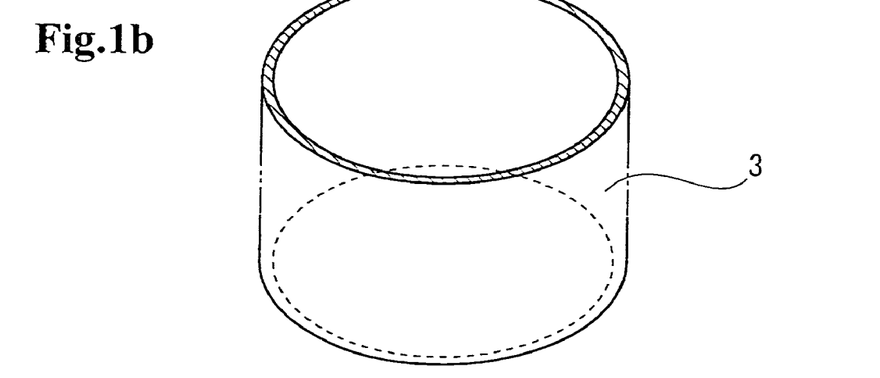
FIG. 1b shows a perspective view of an absorbent-containing layer.
Figure 1C:
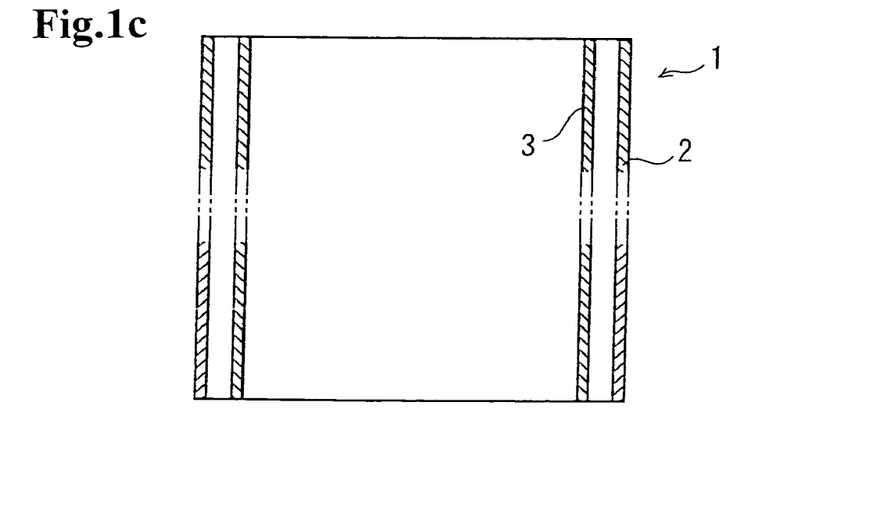
FIG. 1c shows an axial sectional view of the fluid cleaning filter.
Figure 2A:
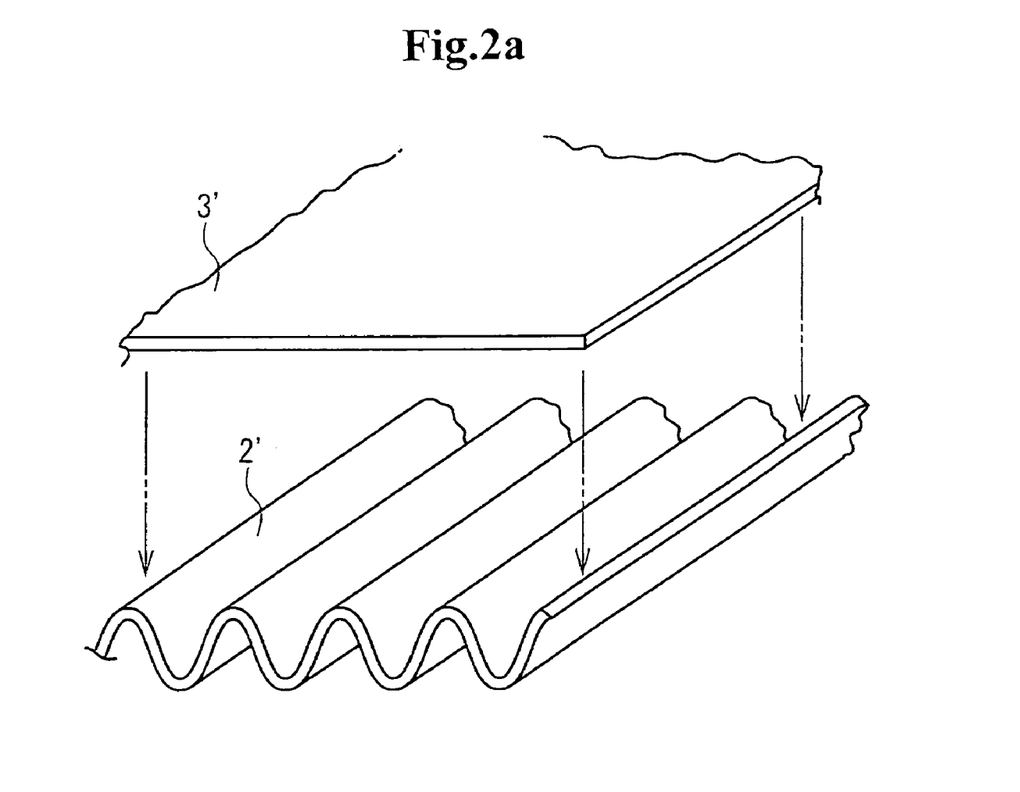
Figure 2B:
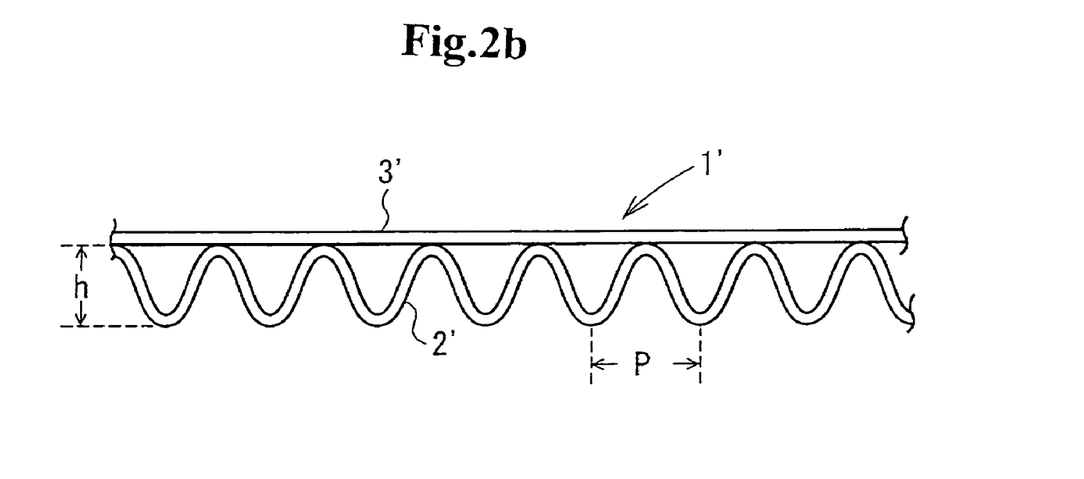
Figure 3:
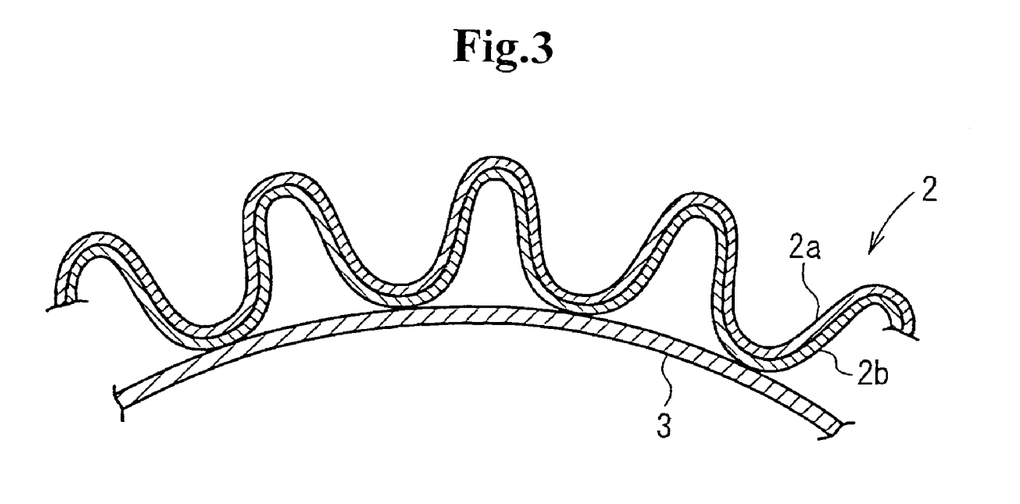
FIG. 3 is an enlarged sectional view of a fluid cleaning filter.
Figure 4:
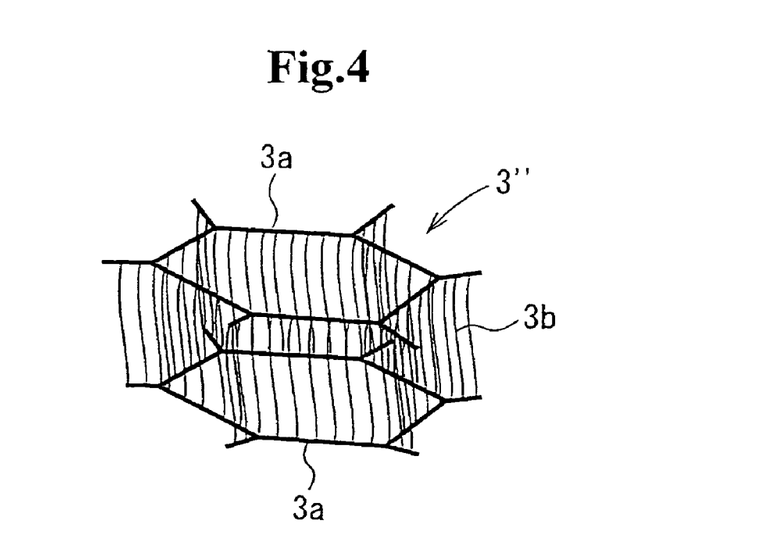
FIG. 4 is a perspective view of a three-dimensional fibrous skeletal structure.
Figure 5:
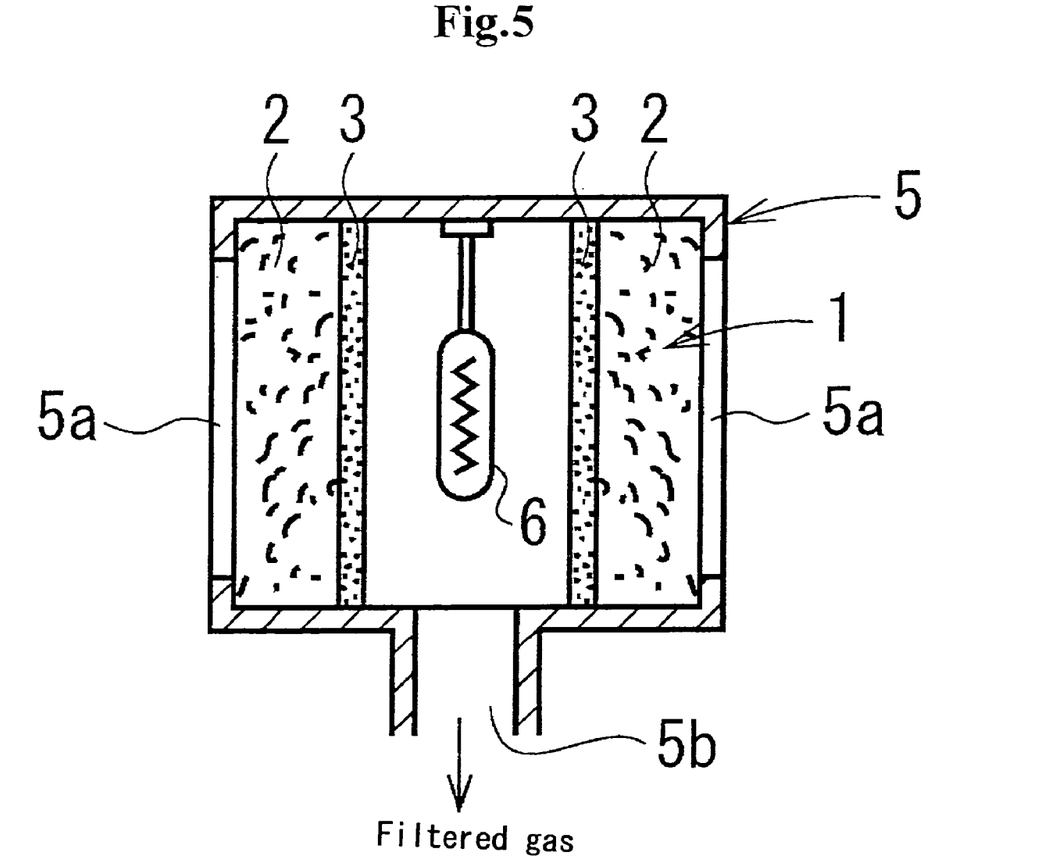
FIG. 5 is a schematic sectional view of a filter device according to an embodiment of the present invention.

FIGS. 1a and 1b show perspective views of a pleated substrate and an absorbent-containing layer (active carbon-containing layer) of a fluid cleaning filter, respectively. FIG. 1c shows a sectional view of the fluid cleaning filter taken along the axis thereof. FIGS. 2a and 2b illustrate of a manner of production of the fluid cleaning filter, respectively. FIG. 3 is an enlarged sectional view showing a part of the fluid cleaning filter. FIG. 4 is an enlarged perspective view of a three-dimensional fibrous skeletal structure. FIG. 5 is a sectional view of a filter device according to an embodiment of the present invention.

A fluid cleaning filter 1 has a cylindrical pleated substrate 2 and an active carbon-containing layer 3 as a cylindrical absorbent-containing layer located inside the cylindrical pleated substrate 2 coaxially.

In FIGS. 1a-1c, the pleated substrate 2 and the active carbon-containing layers 3 are separated from each other, while the flat sheet-like active carbon-containing layer 3' is overposed on the corrugated sheet-like pleated substrate 2' to compose a flat filter 1', shown as FIGS. 2a and 2b, and then the flat filter 1' is configured into a cylindrical shape in such a manner that the pitch direction between the pleats of the pleated substrate 2' is oriented to the circumferential direction of the cylinder, as shown in FIG. 3.

The pleated substrate 2 consists of polyurethane foam having a three-dimensional network skeletal structure, preferably a regular dodecahedral skeletal structure, the structure forming myriad cells (pores) in the polyurethane foam. The number of the cells is preferable to be in a range of 6 to 80 PPI, particularly of 9 to 50 PPI. When the number of the cells is less than 6 PPI, the pressure loss increases, while when the number of cells is more than 80 PPI, the efficiency of collecting and capturing dust decreases.

The thickness of the sheet-like polyurethane foam to be configured into a pleated shape is preferable to be in a range of 1 to 10 mm, particularly of 2 to 5 mm. When the thickness of the polyurethane foam is smaller than 1 mm, the efficiency of collecting and capturing dust and the strength of the filter might become insufficient, while when the thickness of the polyurethane foam exceeds 10 mm, the pressure loss increases and the pleated substrate becomes too bulky.

The polyurethane foam sheet may be configured into a pleated shape by conventional procedure using an accordion pleating machine or the like.

The height of each pleat (h) and the pitch between the neighboring pleats (p) in the corrugated sheet-like pleated substrate 2' prepared by configuring the polyurethane foam sheet into a pleated shape are selected in consideration of the objective, application and allowable pressure loss of the fluid cleaning filter. In usual cases, the height h is preferably in a range of 3 to 150 mm, and the pitch p is preferably in a range of 5 to 50 mm. When the height of the pleats of the pleated substrate 2' is above this range, the resulted pleated substrate 2 becomes bulky and thus the handleability thereof becomes bad, while when the height h is below this range, the efficiency of collecting and capturing dust thereof does not increase sufficiently. When the pitch p is below this range, the configuration thereof can not carry out easily and the pressure loss becomes large, while when the pitch p is above this range, the efficiency of collecting and capturing dust does not increase sufficiently.

The pleated substrate 2 may be configured into not only round shape but also oval shape, angular shape (especially polyangulaer shape), and any suitable shapes. The pleated substrate 2 may be applied with, for example, polyurethane hot-melt adhesives to fix the pitch thereof, if necessary.

The polyurethane foam may be, but not limited to, polyether-urethane foam or polyester-urethane foam.

Figure 7:
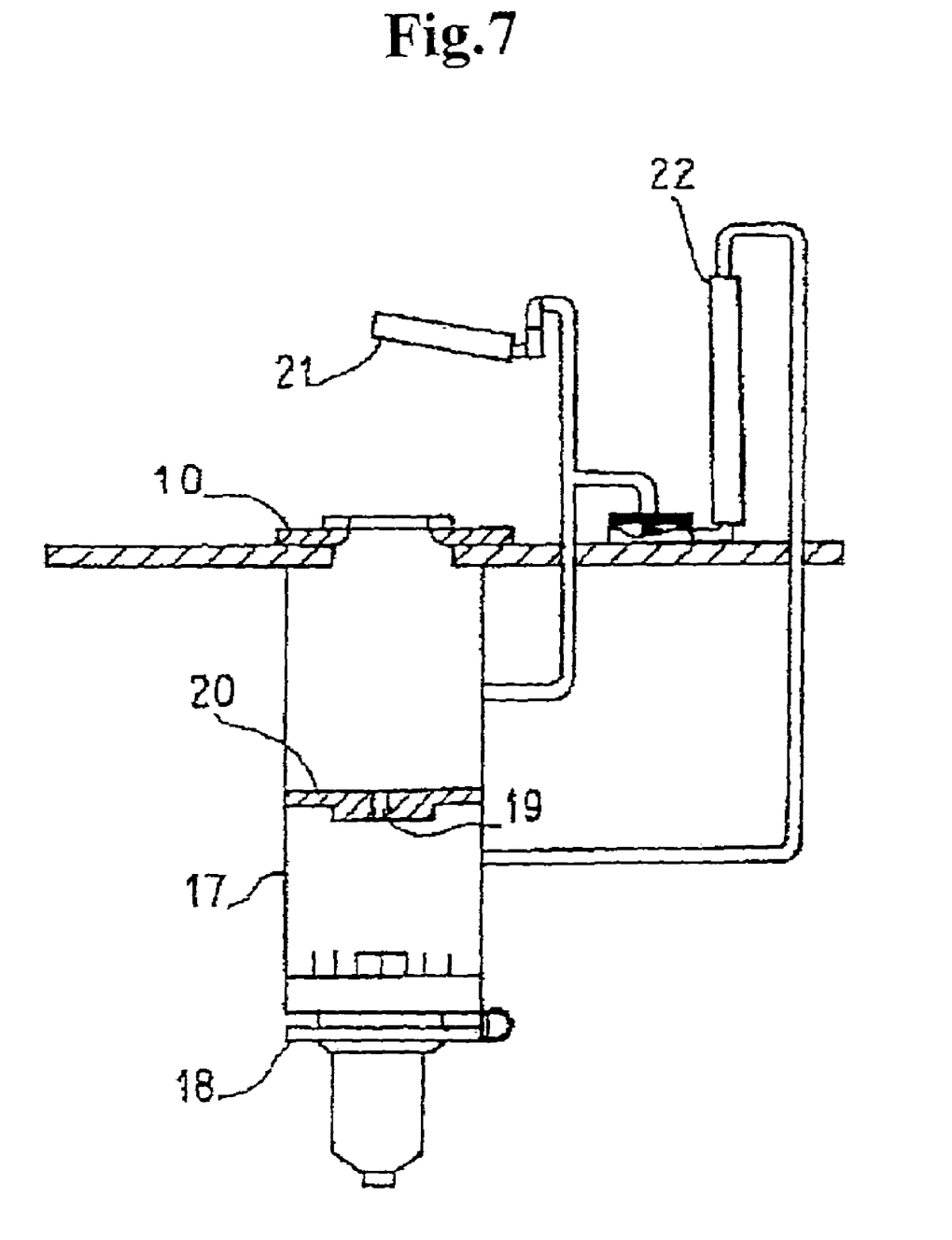
FIG. 7 is a sectional view of a airflow test equipment.

The air permeability ($cm^3$ /$cm^2$ /sec) of the polyurethane foam having a thickness of 10 mm is preferable to be 150 or more, particularly 250 or more, as measured by a FRAGILE type testing apparatus as specified in the Standard JIS L 1004-1972 (Testing Method for Cotton Fabrics) as shown in FIG. 7. The major components of the FRAGILE type testing apparatus shown in FIG. 7 include a cylinder 17 on which a test filter 10 is receivable on the top thereof, a forced draft fan 18 provided at the bottom of the cylinder 17, a partition 20 provided inside the cylinder 17 at the intermediate height of the latter and having a hole 19 formed therein, an inclined barometer 21 and an upright barometer 22. The inclined barometer 21 is adjusted to read a water-column pressure of 1.27 cm. An air passage through the test filter 10 or air permeability thereof is determined based on a pressure indicated on the vertical barometer 22 when the inclined barometer 21 reads the preset water-column pressure of 1.27 cm, and on the type of the hole 19 in the partition 20 used in this measurement.

The pleated substrate can be made by pleating a single layer of the polyurethane foam. However, the pleated substrate may be made by pleating the polyurethane foam layer with an antibacterial function, or a lamination of the polyurethane foam layers having different cell densities.

The polyurethane foam may be provided with a filtering medium layer made of fiber material thereon. Preferably used as the fiber material are synthetic fibers made of polyester, polyamide, polypropylene, polyethylene and acryl, and glass fibers. Preferably employed as the filtering medium layer are a layer made of nonwoven fabric, and a layer consisting of a netting as a core material thereof and nonwoven fabric interlocked to the netting. The example of the latter is a dust filter (EB-04HZ5, having a mass of 20 g/m$^2$, available from Mitsui Petrochemical), which consists of a resin netting made of polypropylene as a core material and polypropylene nonwoven fabric interlocked with the netting.

In case of the filtering medium layer made of nonwoven fabric, for example, fibers such as polypropylene fibers, polyester fibers, polyamide fibers, polyethylene fibers, polyether fibers, acryl fibers and glass fibers are formed into nonwoven fabric by a span-bond process or melt-blow process. In this case, the mass of the fiber material is preferable, but not limited, to be in a range of 15 to 150 g/m$^2$, particularly of 30 to 60 g/m$^2$, on average. The fiber material is preferably applied with a needle-punch process in order to improve the permeability thereof.

The fiber material may be electrostatically charged by a heat-electret process. In this process, the material is electrostatically charged by first heating the material to the softening range thereof, and then cooling the material while applying high direct voltage thereto. The fiber material is significantly improved in efficiency of collecting fine particles by this electrostatically charging process. The fiber material may be electrostatically charged by any suitable process other than the heat-electret process, such as a process in which high voltage is applied to the material by corona discharge, a process in which electron rays of 10 to 40 eV are irradiated to the material, and a process in which the material is subjected to a static magnetic field.

Preferably used as the absorbent-containing layer is, for example, a material (substrate) having fluid-permeability, including gas-permeability, and carrying an absorbent such as active carbon. The active carbon is preferably employed as the absorbent, however, any suitable absorbent such as zeolite may be employed. Any active carbon including coconut shell active carbon, wood active carbon, petroleum pitch active carbon may be employed.

Preferably used as the material (substrate) having gas-permeability is that made of synthetic fibers and/or glass fibers. The examples of the synthetic fibers are polyester fibers, polyamide fibers, polypropylene fibers, polyethylene fibers and acryl fibers.

The absorbent is preferably held in the material (substrate) in such a manner that a binder is applied to the material by spray, impregnation or the like firstly, and then absorbent in a shape of powder, granule or a mixture thereof is brought into contact with the binder to adhere and fix the absorbent to the material. However, the absorbent may be held in the material by impregnating a slurry of the absorbent such as active carbon into the material and then drying it, or by premixing the absorbent prior to the formation of the material. The examples of the binder are hot-melt adhesives, colloidal silica inorganic binders including silica sol, water-glass (a concentrated solution of sodium silicate), and binders having stickiness or adhesiveness including acryl binder, urethane binder, SBR binder, NBR binder, and chloroprene binder.

The absorbent-containing layer is preferably configured into a flat sheet-like absorbent-containing layer 3' as shown in FIGS. 2a and 2b. The flat sheet-like absorbent-containing layer 3' is preferably overlaid onto the corrugated sheet-like pleated substrate 2' via a binder to compose the flat sheet-like filter 1', and then configured into a cylindrical shape together with the pleated substrate 2'. The absorbent-containing layer 3' and the pleated substrate 2' may be configured into a cylindrical shape before or after the binder cures.

The material (substrate) may carry a catalyst, besides the absorbent such as active carbon, to decompose substances absorbed by the absorbent. Alternatively, the absorbent may carry the catalyst. In case that the absorbent carries the catalyst, substances absorbed by the absorbent is effectively decomposed.

Preferably used as the catalyst are oxidizing or reducing catalysts including precious metal or base metal, and photocatalysts including titanium oxide.

The catalyst in a form of powder, granule or mixture thereof is suitable to be applied to the material (substrate) via a binder. In case that the catalyst is formed by vapor deposition or deposition from a liquid phase, the catalyst can be applied to the material having gas-permeability directly or active carbon. The photocatalyst may be applied to the material by using titanium oxide having an anatase type three-dimensional crystalline structure, or using a dispersion containing a natural or synthetic chemical absorbent including zeolite and $SiO_2$.

Hereinafter the examples of the material having gas-permeability and the absorbent-containing layer will be described with reference to FIG. 4.

The material having gas-permeability has a three-dimensional network skeletal structure 3" in which a pair of two-dimensional network skeletal structures 3a, 3a having a hexagonal network are disposed in parallel to each other at a cirtain spacing and connected together with myriad connecting threads 3b.

The fiber material of the three-dimensional fibrous skeletal structure 3" are suitably selected according to the application of the filter. The examples of the fiber material are synthetic fibers such as polyester fibers, polyamide fibers, polypropylene fibers, polyethylene fibers and acryl fibers, and one or more are selected from among these fiber materials to compose the three-dimensional fibrous skeletal structure 3". The polyester fibers, polyamide fibers, polypropylene fibers and the composite fibers consisting of two or more types of fibers selected from among them are preferable for composing the three-dimensional fibrous skeletal structure 3" in view of workability during formation of the three-dimensional fibrous skeletal structure 3", workability of the deodorizing filter, and the durability of the filter.

The two-dimensional network skeletal structure 3a composing the three-dimensional network skeletal structure 3" may be made from one single fiber or twisted fibers formed by twisting plural fibers to have a cirtain thickness. The twisted fibers formed by twisting plural fibers to have a cirtain thickness enable to improve the amount of retainment of the absorbent applied by impregnating a absorbent slurry into the two-dimensional network skeletal structure 3a as will be described later.

The diameter of the fiber composing the two-dimensional network skeletal structure 3a is preferable, but not limited, to be in a range of 0.001 to 0.5 mm, particularly of 0.01 to 0.1 mm, in usual cases. The two-dimensional network skeletal structure 3a may be composed of twisted fibers in which about 10 to 100 fibers each having 5 to 1000 denier, preferably 100 to 500 denier are twisted together.

The two-dimensional network skeletal structure 3a is in a net-like configuration as shown in FIG. 4. The shape of each lattice of the two-dimensional network skeletal structure 3a may be triangular, square, pentagonal, hexagonal or further polygonal. The two-dimensional network skeletal structure 3a having a hexagonal lattice configuration is preferably employed so as to compose a filter having honeycomb structure, thereby improving form stability thereof during work and reducing the pressure loss at the time of using the filter effectively.

The diameter of the lattice of the two-dimensional network skeletal structure 3a is suitably selected according to the application of the filter. In usual cases, the diameter of the lattice is preferable, but not limited, to be in a range of 1 to 15 mm, more preferably of 4 to 7 mm. When the diameter of the lattice is less than 1 mm, the pressure loss might increases in some applications, while when the diameter of the lattice is more than 15 mm, the contact efficiency of gas components and the absorbent might be reduced, thereby reducing the efficiency of gas elimination in some applications.

A pair of the two-dimensional network skeletal structures 3a, 3a compose the front and rear sides of the three-dimensional fibrous skeletal structure 3', respectively. In usual cases, both of the two-dimensional network skeletal structures 3a, 3a are preferable to have substantially the same fiber diameter, the same shape of lattice and the same lattice diameter, that is, substantially the same configuration. However, the two-dimensional network skeletal structures 3a, 3a may be different from each other in configuration in some applications.

The two-dimensional network skeletal structures 3a, 3a are disposed in parallel to each other at a cirtain spacing and connected together with myriad connecting threads 3b. The distance between the two-dimensional network skeletal structures 3a, 3a corresponds to the thickness of the absorbent-containing layer. The distance between the two-dimensional network skeletal structures 3a, 3a is suitably selected according to the application, and in usual cases, it is preferable, but not limited, to be in a range of 2 to 30 mm, more preferably of 5 to 20 mm.

The connecting thread 3b connecting the two-dimensional network skeletal structures 3a, 3a together may be made of different fiber material than that of the two-dimensional network skeletal structures 3a, 3a. However, the connecting thread is preferable to be made of the same fiber material as that of the two-dimensional network skeletal structures 3a, 3a in usual cases. Myriad connecting threads are provided between the two-dimensional network skeletal structures 3a, 3a, wherein the connecting threads 3b may be isolated from each other or may be composed of stitches of one or more common thread weaving the two-dimensional network skeletal structures 3a, 3a.

The thickness of the connecting threads 3b is suitably selected according to the applications of the filter. In usual cases, the thickness of the connecting thread 3b is preferable, but not limited, to be in a range of 5 to 1000 denier, more preferably of 100 to 500 denier. A connecting thread 3b having a thickness of smaller than 5 denier is poor in strength for connecting the two-dimensional network skeletal structures 3a, 3a, and thus might cause limpness of the three-dimensional fibrous skeletal structure 3', while a connecting thread having a thickness of larger than 1000 denier might be hard to weave the two-dimensional network skeletal structures 3a, 3a, thereby making it difficult to construct the three-dimensional fibrous skeletal structure 3".

The absorbent-containing layer 3' is composed by applying a absorbent to the three-dimensional fibrous skeletal structure 3".

The absorbent may be applied to the three-dimensional fibrous skeletal structure 3" by any suitable manner. For example, the absorbent may be applied to the three-dimensional fibrous skeletal structure 3" in such a manner that firstly a slurry of the absorbent is prepared by mixing the absorbent and a binder and then the slurry is impregnated into the three-dimensional fibrous skeletal structure 3". Alternatively, the absorbent may be applied to the three-dimensional fibrous skeletal structure 3" in such a manner that firstly a binder layer is formed on the three-dimensional fibrous skeletal structure 3" by impregnating only a binder into the three-dimensional fibrous skeletal structure 3" and then the absorbent is applied to the binder layer. Further alternatively, the absorbent may be applied to the three-dimensional fibrous skeletal structure 3" in such a manner that firstly a slurry of the absorbent prepared by mixing the absorbent and a binder is impregnated into the three-dimensional fibrous skeletal structure 3" and then the same absorbent or another deodorizer is further applied to the slurry before the binder cures.

The examples of the binder to fix the absorbent to the three-dimensional fibrous skeletal structure 3" are colloidal silica inorganic binders including silica sol, water glass (a concentrated solution of sodium silicate), etc. When the working temperature of the filter is relatively low, binders having stickiness or adhesiveness including acryl binder, urethane binder, SBR binder, NBR binder and chloroprene binder may be employed.

The fluid cleaning filter of the present invention can be widely used in, for example, an aircleaner, room-air conditioner, especially vehicular one, etc. The fluid cleaning filter of the present invention has a good efficiency of collecting dust and reduced pressure loss, so that it can clean a fluid such as air to a high degree effectively.

FIG. 5 is a schematic sectional view of an air filter device equipped with the fluid cleaning filter according to an embodiment of the present invention.

The filter device shown in FIG. 5 has a casing 5 having an air inlet 5a and a suction outlet 5b, and the fluid cleaning filter 1 located in the casing 5. An ultraviolet lamp 6 as a light irradiating means is located inside the fluid cleaning filter 1. The absorbent-containing layer 3 of the fluid cleaning filter 1 carries a photocatalyst. Substances absorbed by the absorbent are decomposed by the decomposition action of the photocatalyst due to the irradiation of ultraviolet light from the lamp 6, so that the absorbent is prevented from being saturated with the absorbed substances, thereby providing a good efficiency of deodorization for a long time.

Hereinafter, the present invention will be described in detail with reference to examples, however, it should be noted that the present invention is not limited to the following examples.

EXAMPLE 1

[Pleated Substrate]

A sheet-like polyurethane foam having a three-dimensional network skeletal structure of 5 mm in thickness and 250 mm×1500 mm in other dimensions, and 50 PPI in cell density (HR-50, available form Bridgestone) was configured into a corrugated sheet-like pleated substrate 2' having pleats of 30 mm in height h, 10 mm in pitch p and 250 mm in length by using an accordion pleating machine.

[Layer Containing Active Carbon]

Particles of titanium oxide having an anatase crystalline structure having particle diameters of 5 to 50 nm were applied to particles of spherical active carbon derived from petroleum pitch having particle diameters of 600 to 1000 μm in such a manner that a sol prepared by dispersing the particles of titanium oxide into water was firstly impregnated into the particles of spherical active carbon and then dried at a temperature of 110° C. for 30 minutes. The amount of the photocatalyst is 1.0 to 1.5% by weight to the active carbon.

A pair of two-dimensional network skeletal structures 3a, 3a were prepared in such a manner that fibers having an average thickness of 1 mm each of which had been prepared by twisting 48 polyester fibers of 250 denier were braided into a net to form myriad hexagonal lattices having an average inner diameter of 5.5 mm in the major axial direction and an average inner diameter of 3.2 mm in the minor axial direction. The two-dimensional network skeletal structures 3a, 3a were disposed in parallel to each other at a spacing of 7 mm and connected together with polyester monofilaments of 150 denier so as to construct an air-permeable material consisting of a three-dimensional fibrous skeletal structure as shown in FIG. 4.

A polyester moisture-curing reactive urethane hot-melt adhesive was impregnated into the front side, rear side and inside of the three-dimensional fibrous skeletal structure uniformly in an amount of 30 to 50 g/l with a roll coater to prepare the three-dimensional fibrous skeletal structure 3".

After that, the particles of active carbon where the photocatalyst was carried thereon were fed and applied into the front side, rear side and inside of the three-dimensional fibrous skeletal structure 3" to prepare the layer 3' having gravity per unit area of 1800 g/m² and containing the active carbon where the photocatalyst was carried.

[Fluid Cleaning Filter]

The active carbon-containing layer 3' was overlaid on the pleated substrate 2' via a hot-melt adhesive. The active carbon-containing layer 3' and the pleated substrate 2' was wound together into a cylindrical shape and then heated to bond with each other, thereby preparing the fluid cleaning filter 1.

The fluid cleaning filter was tested as to pressure loss and efficiency of dust collection as follows.

[Initial Pressure Loss]

Figure 6:
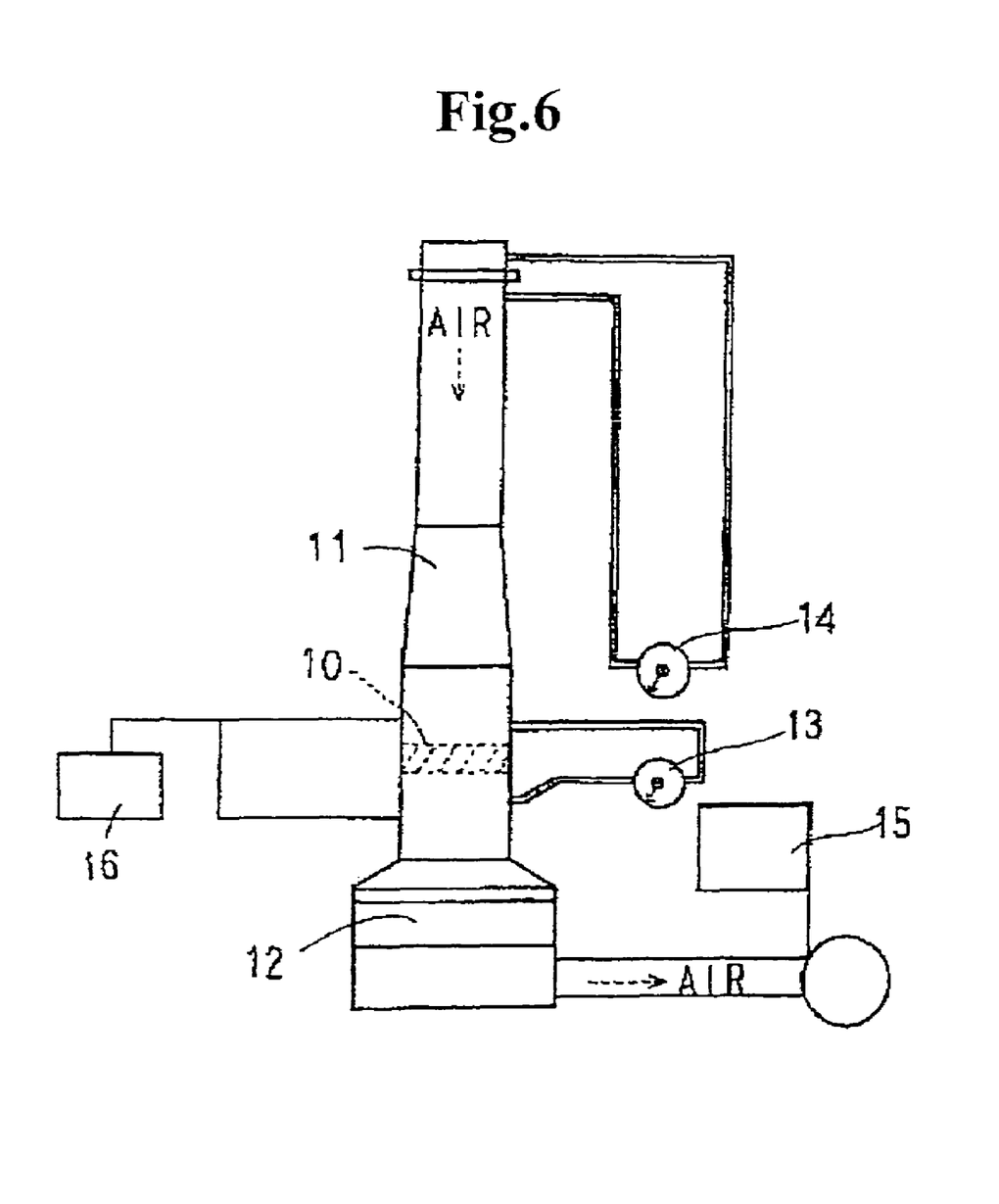
FIG. 6 is a schematic side view of a test equipment used for measuring initial pressure loss and dust capturability in Example 1.

For measurement of the pressure loss and dust collection efficiency, a measuring device shown in FIG. 6 was used. The device has a wind tunnel 11, fan 12, pressure loss meter 13, wind speed indicator 14, control panel 15, and a particle counter 16. In the wind tunnel 11, an air filter 10 under test was placed between the upstream and downstream probes of the pressure loss meter 13, as well as between the upstream and downstream probes of the particle counter 16. Air flow at a speed of 3 m/sec was created by the fan 12. For determination of the pressure loss through the filter 10, the wind pressure was measured upstream and downstream of the filter 10, by the respective probes of the pressure loss meter 13. The difference between the measured wind pressures was calculated and indicated on the pressure loss meter 13. This measured difference represents the pressure loss through the filter 10. For determination of the dust collection efficiency of the filter 10, dust particles of 1 μm or more in air were counted upstream and downstream of the filter 10 by the respective probes of the particle counter 16. The dust particles were counted per 0.01 ft³. For this testing, the atmosphere in the laboratory room was measured. The inside dimensions of the portion of the wind tunnel 11 where the test filter 10 was place was 250×250 mm.

[Dust Collection Efficiency]

In the measuring device shown in FIG. 6, airflow at a speed of 1 m/sec was created by the fan 12 and JIS-15 type of dust particles were supplied into the wind tunnel 11 at a rate of 0.7 g/min. The test was continued until the pressure loss rose 15 mm Ag (147 Pa) above the initial pressure loss, and then the weight of the dust captured by the filter 10 was measured by an electronic balance which can measure a weight with a decimal place.

It becomes apparent from the results of the above tests that the filter had a good efficiency of dust collection and was reduced in pressure loss. Further, it became apparent that the filter exhibited the deodorizing efficiency for a long time.

A comparative filter was prepared in the same manner as the aforementioned exemplary filter except that the comparative filter was remained in a flat sheet-like shape without winding it into a cylindrical shape.

The exemplary cylindrical filter and the comparative flat sheet-like filter were measured in pressure loss in respect to various air flow rates. In this measurement the pressure loss of the cylindrical filter was always lower than that of the flat sheet-like filter.

These filters were also measured in dust collecting efficiency. It became apparent from this measurement that these filters exhibited a good dust collecting efficiency in spite of a low pressure loss.

The exemplary cylindrical filter was located in a casing as shown in FIG. 5. The efficiency of collecting and capturing dust of the filter was measured by filtering four types of air A-D containing toluene, acetaldehyde, $NO_2$ and $SO_2$, respectively. The testing conditions were as follows.

[Content of Ingredient in Air]
air A: toluene 100 ppm
air B: acetaldehyde 50 ppm
air C: $NO_2$ 20 ppm
air D: $SO_2$ 15 ppm

[Ultraviolet Lamp]
352 nm peak-black light (ETD 15BLB, available from Toshiba Lightech), UV power: 1.8 W, 4.4 mW/cm².

[Means for Air Supply and UV Irradiation]
Firstly, the sample air was supplied at a rate of 1L/min for 150 minutes (first air supply).

Secondly, the first air supply was stopped and then UV light was irradiated to the filter for 120 minutes.

After that, the sample air was supplied again of 1L/min for 150 minutes (second air supply)

The rate of removal of each ingredient in air is shown in Tables 1-4. The rate of regeneration due to the UV light irradiation, that is, the percentage of the removal rate in the second air supply to that in the first air supply is also shown in Tables 1-4.

TABLE 1

Removal rate and regeneration rate of toluene

| time of air supply (min) | removal rate (%) | | regeneration rate (%) |
|---|---|---|---|
| | first air supply | second air supply | |
| 5 | 100 | 100 | 100 |
| 15 | 100 | 100 | 100 |
| 30 | 100 | 100 | 100 |
| 60 | 100 | 100 | 100 |
| 90 | 100 | 98.7 | 98.7 |
| 120 | 100 | 98.7 | 98.7 |
| 150 | 100 | 98.7 | 98.7 |

TABLE 2

Removal rate and regeneration rate of acetaldehyde

| time of air supply (min) | removal rate (%) first air supply | removal rate (%) second air supply | regeneration rate (%) |
|---|---|---|---|
| 5 | 100 | 75 | 75.0 |
| 15 | 100 | 70 | 70.0 |
| 30 | 100 | 50 | 50.0 |
| 60 | 71.4 | 37.5 | 52.5 |
| 90 | 57.1 | 25 | 43.8 |
| 120 | 42.8 | 0 | 0.0 |
| 150 | 28.5 | 0 | 0.0 |

TABLE 3

Removal rate and regeneration rate of $NO_2$

| time of air supply (min) | removal rate (%) first air supply | removal rate (%) second air supply | regeneration rate (%) |
|---|---|---|---|
| 5 | 100 | 100 | 100 |
| 15 | 100 | 100 | 100 |
| 30 | 100 | 100 | 100 |
| 60 | 100 | 100 | 100 |
| 90 | 100 | 100 | 100 |
| 120 | 100 | 100 | 100 |
| 150 | 100 | 100 | 100 |

TABLE 4

Removal rate and regeneration rate of $SO_2$

| time of air supply (min) | removal rate (%) first air supply | removal rate (%) second air supply | regeneration rate (%) |
|---|---|---|---|
| 5 | 100 | 90 | 90.0 |
| 15 | 100 | 80 | 80.0 |
| 30 | 90 | 70 | 77.8 |
| 60 | 80 | 30 | 37.5 |
| 90 | 50 | 20 | 40.0 |
| 120 | 20 | 0 | 0.0 |
| 150 | 0 | 0 | — |

INDUSTRIAL APPLICABILITY

As apprent from the aforementioned results, the present invention provides a fluid cleaning filter having good efficiencies of dust collection and deodorization, besides providing reduced pressure loss.

What is claimed is:

1. A fluid cleaning filter comprising;
a cylindrical pleated substrate configured into a pleated shape so that pleats are provided on an inside and outside of the cylindrical pleated substrate; and
a cylindrical absorbent-containing layer,
wherein the cylindrical pleated substrate is made of polyurethane foam at least a part of which has a three-dimensional network skeletal) structure, and
wherein the cylindrical absorbent-containing layer is disposed on an inner circumferential portion of the cylindrical pleated substrate so as to make intermittent contact with the cylindrical pleated substrate, and the cylindrical pleated substrate and the cylindrical absorbent-containing layer form a cylindrical filter,
wherein the absorbent-containing layer contains a catalyst to decompose substances absorbed by the absorbent, and
wherein the catalyst is a photocatalyst.

2. A fluid cleaning filter as claimed in claim 1, wherein said absorbent is active carbon.

3. A fluid cleaning filter as claimed in claim 1, wherein the absorbent-containing layer comprises a material having fluid-permeability and the absorbent is held in the material.

4. A fluid cleaning filter as claimed in claim 3, wherein the material has a three-dimensional network skeletal structure having a pair of two-dimensional network skeletal structures which are disposed in parallel to each other at a certain spacing and connected together with threads.

5. A fluid cleaning tiher as claimed in claim 4, wherein die three-dimensional network skeletal structure is made up of polyester fibers, polyamide fibers, polypropylene fibers or composite fibers thereof.

6. A fluid cleaning filter as claimed in claim 1, wherein the pleated substrate comprises the polyurethane foam and a filtering medium layer formed on the surface of the polyurethane foam, the filtering medium layer being made of fibers.

7. A fluid cleaning filter as claimed in claim 6, wherein the fibers are synthetic fibers or glass fibers.

8. A fluid cleaning filter as claimed in claim 6, wherein the fibers are eletrostatically charged.

9. A fluid cleaning filter as claimed in claim 6, wherein the filtering medium layer is located on the surface of the polyurethane foam facing the material.

10. A fluid cleaning filter as claimed in claim 6 wherein the filtering medium layer has a non woven fabric layer.

11. A fluid cleaning filter as claimed in claim 10, wherein the filtering medium layer has a net made of fibers and said nonwoven fabric layer interlocked with the net.

12. A fluid cleaning filter as claimed in claim 11, wherein the pleated substrate is configured into a cylindrical shape in such a manner that the pitch direction between the pleats thereof is oriented to the circumferential direction ot the cylinder, and
the absorbent-containing layer is configured into cylindrical shape coaxially with respects to the cylindrical pleated substrate.

13. A fluid cleaning filter as claimed in claim 1, wherein the density of cells in the polyurethane form is in a range of 6 to 80 PPI.

14. A filter device equipped with a fluid cleaning filter as claimed in claim 1.

15. A filter device as claimed in claim 14, wherein the filter device is further equipped with a light irradiating means to irradiate light to the absorbent-containing layer.

16. A filter device claimed in claim 15, wherein the light includes ultraviolet light.

17. A filter device as claimed in claim 1, wherein the contact is made in a substantially uniform manner with the absorbent-containing layer and peak areas of the pleated substrate.

* * * * *